United States Patent
Makin et al.

(10) Patent No.: US 7,883,468 B2
(45) Date of Patent: Feb. 8, 2011

(54) MEDICAL SYSTEM HAVING AN ULTRASOUND SOURCE AND AN ACOUSTIC COUPLING MEDIUM

(75) Inventors: Inder Raj S. Makin, Loveland, OH (US); T. Douglas Mast, Cincinnati, OH (US); Michael H. Slayton, Tempe, AZ (US); Peter G. Barthe, Phoenix, AZ (US); Jeffrey D. Messerly, Cincinnati, OH (US); Waseem Faidi, Clifton Park, NY (US); Megan M. Runk, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 842 days.

(21) Appl. No.: 10/848,550

(22) Filed: May 18, 2004

(65) Prior Publication Data

US 2005/0261586 A1 Nov. 24, 2005

(51) Int. Cl.
*A61B 8/00* (2006.01)
(52) U.S. Cl. .............. 600/459; 600/447; 600/472
(58) Field of Classification Search ............ 600/459, 600/439; 604/22; 601/2–4
See application file for complete search history.

(56) References Cited

U.S. PATENT DOCUMENTS

| | | | |
|---|---|---|---|
| 3,168,659 A * | 2/1965 | Bayre et al. ............... | 310/337 |
| 3,902,501 A | 9/1975 | Citron et al. | |
| 3,927,557 A * | 12/1975 | Viertl ........................ | 73/607 |
| 4,315,514 A | 2/1982 | Drewes et al. | |
| 4,323,077 A | 4/1982 | Smith | |
| 4,396,019 A | 8/1983 | Perry, Jr. | |
| 4,484,569 A | 11/1984 | Driller et al. | |
| 4,646,756 A | 3/1987 | Watnough et al. | |
| 4,748,985 A * | 6/1988 | Nagasaki ................... | 600/445 |
| 4,757,820 A | 7/1988 | Itoh | |
| 4,765,331 A | 8/1988 | Petruzzi et al. | |

(Continued)

FOREIGN PATENT DOCUMENTS

CN    1628615    6/2005

(Continued)

OTHER PUBLICATIONS

Hill, C.R. et al., Lesion Development In Focused Ultrasound Surgery: A General Model, Ultrasound in Med. & Biol., 1994, pp. 259-269, vol. 20, No. 3; Elsevier Science Ltd, New York, USA.

(Continued)

*Primary Examiner*—Brian Casler
*Assistant Examiner*—Jonathan G Cwern

(57) ABSTRACT

An ultrasound medical system has an end effector including a medical ultrasound transducer and an acoustic coupling medium. The acoustic coupling medium has a transducer-proximal surface and a transducer-distal surface. The medical ultrasound transducer is positioned to emit medical ultrasound through the acoustic coupling medium from the transducer-proximal surface to the transducer-distal surface. The end effector is adapted to change a property (such as the shape and/or the temperature) of the acoustic coupling medium during emission, and/or between emissions, of medical ultrasound from the medical ultrasound transducer during a medical procedure on a patient. In one example, such changes are used to change the focus and/or beam angle of the emitted ultrasound during the medical procedure.

10 Claims, 3 Drawing Sheets

U.S. PATENT DOCUMENTS

| | | | |
|---|---|---|---|
| 4,787,394 A | 11/1988 | Ogura | |
| 4,798,215 A | 1/1989 | Turner | |
| 4,818,954 A | 4/1989 | Flachenecker et al. | |
| 4,844,080 A * | 7/1989 | Frass et al. | 600/437 |
| 4,858,613 A * | 8/1989 | Fry et al. | 600/439 |
| 4,932,414 A | 6/1990 | Coleman et al. | |
| 4,937,767 A | 6/1990 | Reuschel et al. | |
| 4,951,653 A | 8/1990 | Fry et al. | |
| 4,955,365 A | 9/1990 | Fry et al. | |
| 4,955,366 A | 9/1990 | Uchiyama et al. | |
| 4,960,107 A | 10/1990 | Aida et al. | |
| 4,960,109 A | 10/1990 | Lele | |
| 4,984,575 A | 1/1991 | Uchiyama et al. | |
| 4,986,275 A | 1/1991 | Ishida et al. | |
| RE33,590 E | 5/1991 | Dory | |
| 5,015,929 A | 5/1991 | Cathignol et al. | |
| 5,036,855 A | 8/1991 | Fry et al. | |
| 5,054,470 A | 10/1991 | Fry et al. | |
| 5,065,740 A | 11/1991 | Itoh | |
| 5,078,144 A | 1/1992 | Sekino et al. | |
| 5,080,101 A | 1/1992 | Dory | |
| 5,080,102 A | 1/1992 | Dory | |
| 5,095,907 A | 3/1992 | Kudo et al. | |
| 5,117,832 A | 6/1992 | Sanghvi et al. | |
| 5,143,073 A | 9/1992 | Dory | |
| 5,143,074 A | 9/1992 | Dory | |
| 5,149,319 A | 9/1992 | Unger | |
| 5,150,711 A | 9/1992 | Dory | |
| 5,150,712 A | 9/1992 | Dory | |
| 5,158,070 A | 10/1992 | Dory | |
| 5,158,071 A | 10/1992 | Umemura et al. | |
| 5,203,333 A | 4/1993 | Nomura | |
| 5,209,221 A | 5/1993 | Riedlinger | |
| 5,238,007 A | 8/1993 | Giele et al. | |
| 5,240,005 A | 8/1993 | Viebach | |
| 5,242,437 A | 9/1993 | Everett et al. | |
| 5,295,484 A | 3/1994 | Marcus et al. | |
| 5,304,115 A | 4/1994 | Pflueger et al. | |
| 5,305,731 A * | 4/1994 | Buchholtz | 601/4 |
| 5,311,869 A | 5/1994 | Okazaki | |
| 5,348,017 A | 9/1994 | Thornton et al. | |
| 5,354,258 A | 10/1994 | Dory | |
| 5,391,140 A | 2/1995 | Schaetzle et al. | |
| 5,391,197 A | 2/1995 | Burdette et al. | |
| 5,402,792 A | 4/1995 | Kimura | |
| 5,409,002 A | 4/1995 | Pell | |
| 5,413,550 A | 5/1995 | Castel | |
| 5,419,335 A * | 5/1995 | Hartmann et al. | 600/472 |
| 5,431,663 A | 7/1995 | Carter | |
| 5,435,304 A | 7/1995 | Oppelt et al. | |
| 5,435,311 A | 7/1995 | Umemura et al. | |
| 5,443,069 A | 8/1995 | Schaetzle | |
| 5,448,994 A | 9/1995 | Iinuma | |
| 5,458,597 A | 10/1995 | Edwards et al. | |
| 5,465,724 A | 11/1995 | Sliwa et al. | |
| 5,471,988 A | 12/1995 | Fujio et al. | |
| 5,474,071 A | 12/1995 | Chapelon et al. | |
| 5,485,839 A | 1/1996 | Aida et al. | |
| 5,492,126 A | 2/1996 | Hennige et al. | |
| 5,500,012 A | 3/1996 | Brucker et al. | |
| 5,501,655 A | 3/1996 | Rolt et al. | |
| 5,514,085 A | 5/1996 | Yoon | |
| 5,514,130 A | 5/1996 | Baker | |
| 5,520,188 A | 5/1996 | Hennige et al. | |
| 5,522,869 A | 6/1996 | Burdette et al. | |
| 5,524,620 A | 6/1996 | Rosenschein | |
| 5,526,815 A | 6/1996 | Granz et al. | |
| 5,526,822 A | 6/1996 | Burbank et al. | |
| 5,540,656 A | 7/1996 | Pflueger et al. | |
| 5,545,195 A | 8/1996 | Lennox et al. | |
| 5,547,459 A | 8/1996 | Kaufman et al. | |
| 5,549,638 A | 8/1996 | Burdette | |
| 5,558,092 A | 9/1996 | Unger et al. | |
| 5,569,241 A | 10/1996 | Edwards | |
| 5,571,088 A | 11/1996 | Lennox et al. | |
| 5,573,497 A | 11/1996 | Chapelon | |
| 5,575,288 A | 11/1996 | Sliwa et al. | |
| 5,575,772 A | 11/1996 | Lennox | |
| 5,575,789 A | 11/1996 | Bell et al. | |
| 5,582,588 A | 12/1996 | Sakurai et al. | |
| 5,588,432 A | 12/1996 | Crowley | |
| 5,590,657 A | 1/1997 | Cain et al. | |
| 5,601,526 A | 2/1997 | Chapelon et al. | |
| 5,620,479 A | 4/1997 | Diederich | |
| 5,624,382 A | 4/1997 | Oppelt et al. | |
| 5,628,743 A | 5/1997 | Cimino | |
| 5,630,837 A | 5/1997 | Crowley | |
| 5,643,179 A | 7/1997 | Fujimoto | |
| 5,649,547 A | 7/1997 | Ritchart et al. | |
| 5,657,760 A | 8/1997 | Ying et al. | |
| 5,665,054 A | 9/1997 | Dory | |
| 5,666,954 A | 9/1997 | Chapelon et al. | |
| 5,676,692 A | 10/1997 | Sanghvi et al. | |
| 5,687,729 A | 11/1997 | Schaetzle | |
| 5,694,936 A | 12/1997 | Fujimoto et al. | |
| 5,697,897 A | 12/1997 | Buchholtz et al. | |
| 5,699,804 A | 12/1997 | Rattner | |
| 5,703,922 A | 12/1997 | Rattner | |
| 5,715,825 A | 2/1998 | Crowley | |
| 5,720,287 A | 2/1998 | Chapelon et al. | |
| 5,722,411 A | 3/1998 | Suzuki et al. | |
| 5,728,062 A | 3/1998 | Brisken | |
| 5,733,315 A | 3/1998 | Burdette et al. | |
| 5,735,280 A | 4/1998 | Sherman et al. | |
| 5,735,796 A | 4/1998 | Granz et al. | |
| 5,738,635 A | 4/1998 | Chapelon et al. | |
| 5,743,862 A | 4/1998 | Izumi | |
| 5,743,863 A | 4/1998 | Chapelon | |
| 5,746,224 A | 5/1998 | Edwards | |
| 5,759,154 A | 6/1998 | Hoyns | |
| 5,759,162 A | 6/1998 | Oppelt et al. | |
| 5,762,066 A | 6/1998 | Law et al. | |
| 5,769,086 A | 6/1998 | Ritchart et al. | |
| 5,769,790 A | 6/1998 | Watkins et al. | |
| 5,771,896 A | 6/1998 | Sliwa et al. | |
| 5,785,705 A | 7/1998 | Baker | |
| 5,788,636 A | 8/1998 | Curley | |
| 5,800,379 A | 9/1998 | Edwards | |
| 5,800,429 A | 9/1998 | Edwards | |
| 5,807,308 A | 9/1998 | Edwards | |
| 5,817,021 A | 10/1998 | Reichenberger | |
| 5,817,049 A | 10/1998 | Edwards | |
| 5,820,580 A | 10/1998 | Edwards et al. | |
| 5,823,962 A | 10/1998 | Schaetzle et al. | |
| 5,836,896 A | 11/1998 | Rosenschein | |
| 5,840,031 A | 11/1998 | Crowley | |
| 5,842,994 A | 12/1998 | TenHoff et al. | |
| 5,860,974 A | 1/1999 | Abele | |
| 5,873,828 A | 2/1999 | Fujio et al. | |
| 5,873,845 A | 2/1999 | Cline et al. | |
| 5,873,902 A | 2/1999 | Sanghvi et al. | |
| 5,876,399 A | 3/1999 | Chia et al. | |
| 5,882,302 A | 3/1999 | Driscoll, Jr. et al. | |
| 5,895,356 A | 4/1999 | Andrus et al. | |
| 5,897,495 A | 4/1999 | Aida et al. | |
| 5,897,523 A | 4/1999 | Wright et al. | |
| 5,925,044 A | 7/1999 | Hofmann et al. | |
| 5,928,169 A | 7/1999 | Schatzle et al. | |
| 5,931,848 A | 8/1999 | Saadat | |
| 5,938,600 A | 8/1999 | Van Vaals et al. | |
| 5,938,608 A | 8/1999 | Bieger et al. | |
| 5,944,663 A | 8/1999 | Kuth et al. | |
| 5,964,755 A | 10/1999 | Edwards | |
| 5,979,453 A | 11/1999 | Savage et al. | |

| | | |
|---|---|---|
| 5,984,881 A | 11/1999 | Ishibashi et al. |
| 5,984,882 A | 11/1999 | Rosenschein et al. |
| 5,993,389 A | 11/1999 | Driscoll, Jr. et al. |
| 5,997,534 A | 12/1999 | Tu et al. |
| 6,001,069 A | 12/1999 | Tachibana et al. |
| 6,004,269 A | 12/1999 | Crowley et al. |
| 6,007,499 A | 12/1999 | Martin et al. |
| 6,022,319 A | 2/2000 | Willard et al. |
| 6,024,718 A | 2/2000 | Chen et al. |
| 6,024,740 A | 2/2000 | Lesh et al. |
| 6,027,449 A * | 2/2000 | Mazess et al. ............ 600/449 |
| 6,033,397 A | 3/2000 | Laufer et al. |
| 6,039,689 A | 3/2000 | Lizzi |
| 6,041,260 A | 3/2000 | Stern et al. |
| 6,042,556 A | 3/2000 | Beach et al. |
| 6,050,943 A | 4/2000 | Slayton et al. |
| 6,066,123 A | 5/2000 | Li et al. |
| 6,071,238 A | 6/2000 | Chapelon et al. |
| 6,071,239 A | 6/2000 | Cribbs et al. |
| 6,083,159 A | 7/2000 | Driscoll, Jr. et al. |
| 6,086,535 A | 7/2000 | Ishibashi et al. |
| 6,086,583 A | 7/2000 | Ouchi |
| 6,088,613 A | 7/2000 | Unger |
| 6,106,469 A * | 8/2000 | Suzuki et al. ............ 600/443 |
| 6,106,517 A | 8/2000 | Zupkas |
| 6,112,123 A | 8/2000 | Kelleher et al. |
| 6,113,558 A | 9/2000 | Rosenschein et al. |
| 6,117,101 A | 9/2000 | Diederich et al. |
| 6,135,963 A | 10/2000 | Haider |
| 6,135,971 A | 10/2000 | Hutchinson et al. |
| 6,138,513 A | 10/2000 | Barabash et al. |
| 6,148,224 A | 11/2000 | Jensen |
| 6,171,248 B1 | 1/2001 | Hossack et al. |
| 6,176,842 B1 | 1/2001 | Tachibana et al. |
| 6,183,469 B1 | 2/2001 | Thapilyal et al. |
| 6,210,330 B1 | 4/2001 | Tepper |
| 6,216,704 B1 | 4/2001 | Ingle et al. |
| 6,217,576 B1 | 4/2001 | Tu et al. |
| 6,231,834 B1 | 5/2001 | Unger et al. |
| 6,352,532 B1 | 3/2002 | Kramer et al. |
| 6,361,531 B1 | 3/2002 | Hissong |
| 6,371,903 B1 | 4/2002 | Blanc et al. |
| 6,379,320 B1 | 4/2002 | Lafon et al. |
| 6,394,949 B1 | 5/2002 | Crowley et al. |
| 6,425,867 B1 | 7/2002 | Vaezy et al. |
| 6,482,178 B1 | 11/2002 | Andrews et al. |
| 6,508,774 B1 | 1/2003 | Acker et al. |
| 6,512,957 B1 | 1/2003 | Witte |
| 6,521,211 B1 | 2/2003 | Unger et al. |
| 6,533,726 B1 | 3/2003 | Lizzi et al. |
| 6,546,934 B1 | 4/2003 | Ingle et al. |
| 6,575,956 B1 | 6/2003 | Brisken et al. |
| 6,599,245 B1 | 7/2003 | Ma et al. |
| 6,602,251 B2 | 8/2003 | Burbank et al. |
| 6,613,004 B1 | 9/2003 | Vitek et al. |
| 6,618,620 B1 | 9/2003 | Freundlich et al. |
| 6,626,855 B1 | 9/2003 | Weng et al. |
| 6,645,202 B1 | 11/2003 | Pless et al. |
| 6,669,638 B1 | 12/2003 | Miller et al. |
| 6,716,184 B2 | 4/2004 | Vaezy et al. |
| 6,719,694 B2 | 4/2004 | Weng et al. |
| 6,764,488 B1 | 7/2004 | Burbank et al. |
| 6,770,070 B1 | 8/2004 | Balbierz |
| 6,783,524 B2 | 8/2004 | Anderson et al. |
| 6,887,239 B2 | 5/2005 | Elstrom et al. |
| 6,902,536 B2 | 6/2005 | Manna et al. |
| 6,921,371 B2 | 7/2005 | Wilson |
| 6,936,024 B1 | 8/2005 | Houser |
| 6,936,048 B2 | 8/2005 | Hurst |
| 6,974,417 B2 | 12/2005 | Lockwood et al. |
| 7,037,306 B2 | 5/2006 | Podany et al. |
| 7,063,666 B2 | 6/2006 | Weng et al. |
| 7,078,015 B2 | 7/2006 | Unger |
| 2001/0007940 A1 | 7/2001 | Tu et al. |
| 2001/0014805 A1 | 8/2001 | Burbank et al. |
| 2001/0037073 A1 | 11/2001 | White et al. |
| 2002/0065512 A1* | 5/2002 | Fjield et al. ............ 606/27 |
| 2002/0068934 A1 | 6/2002 | Edwards et al. |
| 2002/0072741 A1 | 6/2002 | Sliwa et al. |
| 2002/0087081 A1 | 7/2002 | Serrano et al. |
| 2002/0087083 A1 | 7/2002 | Nix et al. |
| 2002/0111662 A1 | 8/2002 | Iaizzo et al. |
| 2002/0147447 A1 | 10/2002 | Long |
| 2002/0156470 A1 | 10/2002 | Shadduck |
| 2002/0165579 A1 | 11/2002 | Burbank et al. |
| 2002/0183742 A1 | 12/2002 | Carmel et al. |
| 2002/0183771 A1 | 12/2002 | Burbank et al. |
| 2002/0193781 A1 | 12/2002 | Loeb |
| 2003/0004434 A1 | 1/2003 | Greco et al. |
| 2003/0013960 A1 | 1/2003 | Makin et al. |
| 2003/0013971 A1 | 1/2003 | Makin et al. |
| 2003/0018266 A1 | 1/2003 | Makin et al. |
| 2003/0018358 A1 | 1/2003 | Saadat |
| 2003/0028111 A1 | 2/2003 | Vaezy et al. |
| 2003/0040698 A1 | 2/2003 | Makin et al. |
| 2003/0047582 A1 | 3/2003 | Sonnenschein et al. |
| 2003/0073907 A1 | 4/2003 | Taylor |
| 2003/0109786 A1 | 6/2003 | Irioka et al. |
| 2003/0120270 A1 | 6/2003 | Acker |
| 2003/0144593 A1 | 7/2003 | Whitmore et al. |
| 2003/0181900 A1 | 9/2003 | Long |
| 2003/0212331 A1 | 11/2003 | Fenton et al. |
| 2003/0212332 A1 | 11/2003 | Fenton et al. |
| 2003/0220568 A1 | 11/2003 | Hansmann et al. |
| 2003/0225331 A1 | 12/2003 | Diederich et al. |
| 2003/0229293 A1 | 12/2003 | Hibner et al. |
| 2004/0006336 A1 | 1/2004 | Swanson |
| 2004/0030268 A1 | 2/2004 | Weng et al. |
| 2004/0143252 A1 | 7/2004 | Hurst |
| 2004/0236375 A1 | 11/2004 | Redding, Jr. |
| 2004/0254570 A1 | 12/2004 | Hadjicostis et al. |
| 2005/0015107 A1 | 1/2005 | O'Brien |
| 2005/0085726 A1* | 4/2005 | Lacoste et al. ............ 600/439 |
| 2005/0137520 A1 | 6/2005 | Rule et al. |
| 2005/0228286 A1 | 10/2005 | Messerly et al. |
| 2005/0240125 A1 | 10/2005 | Makin et al. |
| 2005/0261585 A1 | 11/2005 | Makin et al. |
| 2005/0261587 A1 | 11/2005 | Makin et al. |
| 2005/0261588 A1 | 11/2005 | Makin et al. |
| 2005/0267488 A1 | 12/2005 | Hare et al. |
| 2006/0052695 A1 | 3/2006 | Adam |
| 2006/0052701 A1 | 3/2006 | Carter et al. |
| 2006/0173348 A1 | 8/2006 | Wilser et al. |
| 2006/0235306 A1 | 10/2006 | Cotter et al. |
| 2007/0021691 A1 | 1/2007 | Nita et al. |
| 2008/0058648 A1 | 3/2008 | Novak et al. |

FOREIGN PATENT DOCUMENTS

| | | |
|---|---|---|
| EP | 1518498 | 3/2005 |
| JP | 06-181923 | 7/1994 |

OTHER PUBLICATIONS

Clare, M.C. et al., MRI Guided Focused Ultrasound Surgery (FUS) of uterine leiomyomas: A Feasibility Study, Workshop on MRI-Guided: Focused Ultrasound Surgery, 2002, Syllabus, International Society for Magnetic Resonance in Medicine.

Vaezy, S. et al., Treatment Of Uterine Fibroid Tumors In A Nude Mouse Model Using High-Intensity Focused Ultrasound, Am J Obstet Gynecol, 2000, pp. 6-11, vol. 183, No. 1.

Cool-tip™ RF Tadio Frequency Ablation System, web page from radionics.com.

Electrosurgical Devices, RF Generator and RITA Base Software, web pages from ritamedical.com.

Chavrier et al., "Modeling of high-intensity focused ultrasound-induced lesions in the presence of cavitation bubbles," J. Acoust. Soc. Am. 108 (1), pp. 432-440 (Jul. 2000).

Watkins et al., "High-intensity focused ultrasound ablation of the kidney in a large animal model," J. Endourol., 11 (3), 191, abstract (Jun. 1997).

Billard, et al., "Effects of Physical Parameters in High Temperature Ultrasound Hyperthermia," Ultrasound in Medicine and Biology, vol. 16, Issue 4, pp. 409-420 (1990).

English language Abstract of JP 06-181923, as provided by the European Patent Office on-line database.

English language machine translation of JP 06-181923, as provided by the Japanese Patent Office on-line service.

Office Action, Chinese Application No. 200680032059.2 (6 pages) (Nov. 6, 2009).

Supplementary European Search Report, European Application No. 06787104.6 (8 pages) (Sep. 16, 2009).

* cited by examiner

MEDICAL SYSTEM HAVING AN ULTRASOUND SOURCE AND AN ACOUSTIC COUPLING MEDIUM

FIELD OF THE INVENTION

The present invention relates generally to ultrasound, and more particularly to an ultrasound medical system having an ultrasound source and an acoustic coupling medium.

BACKGROUND OF THE INVENTION

Known ultrasound medical methods include using ultrasound imaging (at low power) of patients to identify patient tissue for medical treatment and include using ultrasound (at high power), from the same or a different ultrasound transducer, to ablate identified patient tissue by heating the tissue.

Known ultrasound medical systems and methods include deploying an end effector having an ultrasound transducer outside the body to break up kidney stones inside the body, endoscopically inserting an end effector having an ultrasound transducer in the rectum to medically destroy prostate cancer, laparoscopically inserting an end effector having an ultrasound transducer in the abdominal cavity to medically destroy a cancerous liver tumor, intravenously inserting a catheter end effector having an ultrasound transducer into a vein in the arm and moving the catheter to the heart to medically destroy diseased heart tissue, and interstitially inserting a needle end effector having an ultrasound transducer needle into the tongue to medically destroy tissue to reduce tongue volume to reduce snoring.

Conventional ultrasound medical systems include a system having an end effector including a medical ultrasound transducer, a sheath, and a water acoustic coupling medium. The end effector is inserted into a patient, and a balloon portion (which acts as an acoustic window) of the sheath is expanded by increasing water pressure until the balloon portion contacts patient tissue. Then, the medical ultrasound transducer emits medical ultrasound through the balloon portion via the water to image and/or treat the patient tissue.

Still, scientists and engineers continue to seek improved ultrasound medical systems.

SUMMARY OF THE INVENTION

A first expression of an embodiment of the invention is an ultrasound medical system having an end effector including a medical ultrasound transducer and an acoustic coupling medium. The acoustic coupling medium has a transducer-proximal surface and a transducer-distal surface. The medical ultrasound transducer is positioned to emit medical ultrasound through the acoustic coupling medium from the transducer-proximal surface to the transducer-distal surface. The end effector is adapted to change at least one property of the acoustic coupling medium during emission, and/or between emissions, of medical ultrasound from the medical ultrasound transducer during a medical procedure on a patient.

A second expression of an embodiment of the invention is an ultrasound medical system having a controller and an end effector. The end effector includes a medical ultrasound transducer and an acoustic coupling medium. The acoustic coupling medium has a transducer-proximal surface and a transducer-distal surface. The medical ultrasound transducer is positioned to emit medical ultrasound having a focus and a beam angle through the acoustic coupling medium from the transducer-proximal surface to the transducer-distal surface. The end effector is adapted to change at least one property of the acoustic coupling medium during emission, and/or between emissions, of medical ultrasound from the medical ultrasound transducer during a medical procedure on a patient. The controller controls the end effector to change the property to change the focus and/or the beam angle.

A third expression of an embodiment of the invention is an ultrasound medical system having a controller and an end effector. The end effector includes a medical ultrasound transducer, an acoustic coupling medium, and a sheath. The sheath includes an expandable acoustic window, wherein the acoustic coupling medium is placed in direct contact with the medical ultrasound transducer and the acoustic window. The medical ultrasound transducer is positioned to emit medical ultrasound through the acoustic window via the acoustic coupling medium. The controller controls the end effector to change the shape of the acoustic window, by changing the pressure exerted by the acoustic coupling medium against the acoustic window, during emission, and/or between emissions, of medical ultrasound from the medical ultrasound transducer during a medical procedure on a patient.

Several benefits and advantages are obtained from one or more of the expressions of an embodiment of the ultrasound medical system of the invention. The acoustic coupling medium also acts as an acoustic lens, wherein the end effector is adapted to change at least one property (such as the shape and/or the temperature) of the acoustic coupling medium which will change the focus and/or the beam angle of emitted ultrasound, with such changes occurring during emission, and/or between emissions, of ultrasound while performing a medical procedure on a patient.

The present invention has, without limitation, application in conventional endoscopic, laparoscopic, and open surgical instrumentation as well as application in robotic-assisted surgery.

DETAILED DESCRIPTION OF THE INVENTION

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

It is understood that any one or more of the following-described embodiments, examples, etc. can be combined with any one or more of the other following-described embodiments, examples, etc.

Figure 1:
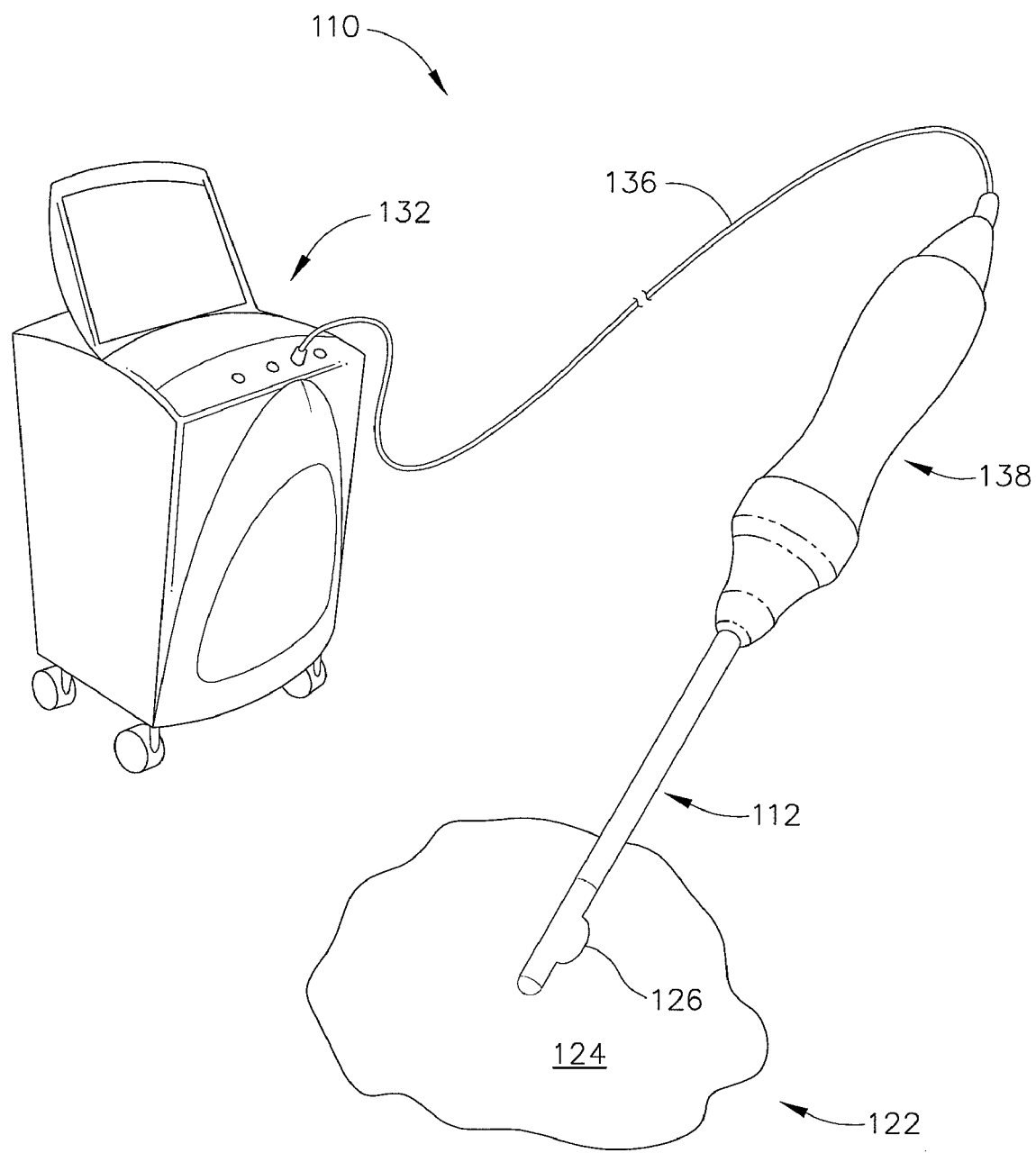
FIG. 1 is a perspective view of a first embodiment of an ultrasound medical system of the invention including a controller and an end effector, wherein the end effector is seen inserted into a patient (only a portion of whom is shown) and has an acoustic window, and wherein the end effector is adapted to change the shape of the acoustic window during a medical procedure by increasing the pressure of an acoustic coupling medium located inside the end effector.
Figure 2:
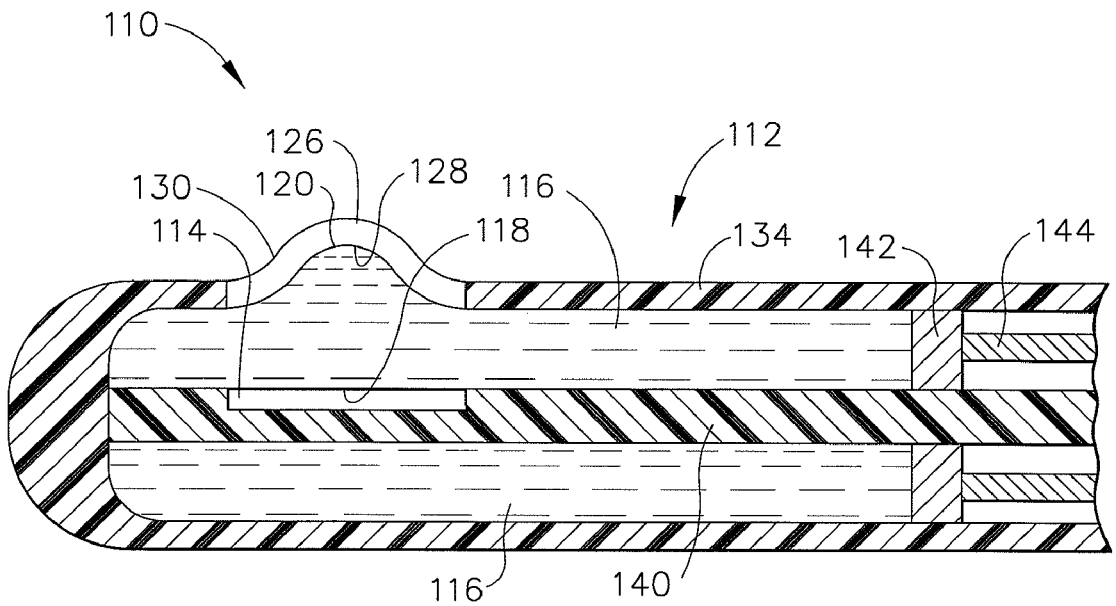
FIG. 2 is a schematic cross-sectional view of the end effector of the ultrasound medical system of FIG. 1, wherein the adaptation of the end effector is shown and includes a movable piston which exerts pressure on the acoustic coupling medium.

Referring now to the drawings, FIGS. 1-2 illustrate an embodiment of the present invention. A first expression of the embodiment of FIGS. 1-2 is an ultrasound medical system 110 comprising an end effector 112 including a medical ultrasound transducer 114 and an acoustic coupling medium 116. The acoustic coupling medium 116 has a transducer-proximal surface 118 and a transducer-distal surface 120. The medical ultrasound transducer 114 is disposed to emit medical ultrasound through the acoustic coupling medium 116 from the transducer-proximal surface 118 to the transducer-distal surface 120. The end effector 112 is adapted to change at least one property of the acoustic coupling medium 116 during emission, and/or between emissions, of medical ultrasound from the medical ultrasound transducer 114 during a medical procedure on a patient 122. The terminology "ultrasound medical system" includes an ultrasound medical imaging system, an ultrasound medical treatment system, and an ultrasound medical imaging and ultrasound medical treatment system. The terminology "medical procedure" includes an imaging procedure, a treatment procedure, and an imaging and treatment procedure.

In an enablement of the first expression of the embodiment of FIGS. 1-2, the at-least-one property includes shape, and the end effector 112 is adapted to change the shape (such as the curvature) of the transducer-distal surface 120 during emission, and/or between emissions, of medical ultrasound from the medical ultrasound transducer 114 during the medical procedure.

Figure 3:
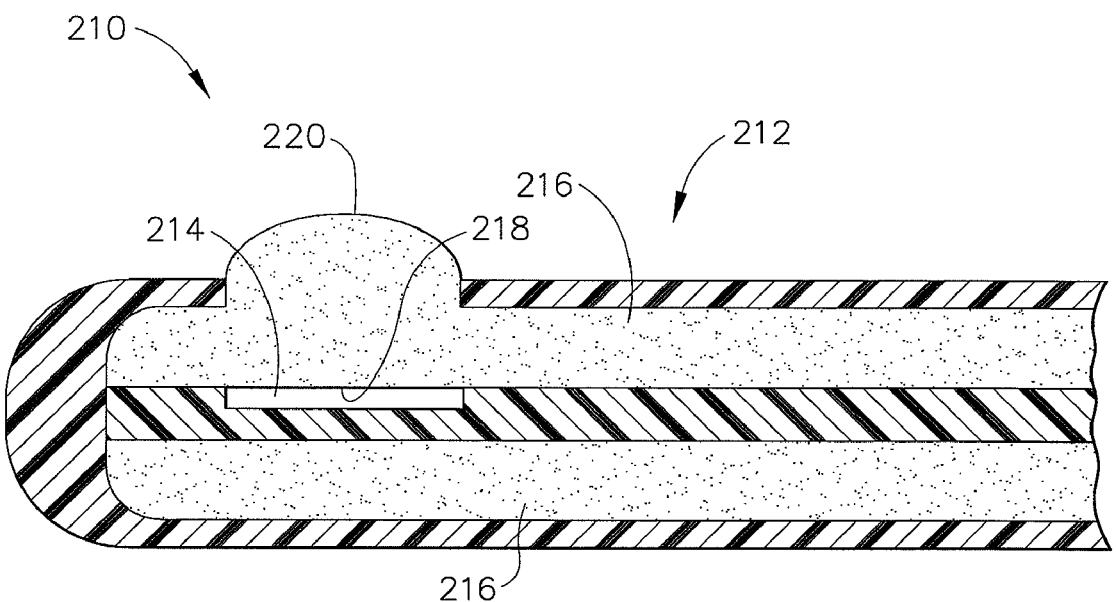
FIG. 3 is a schematic cross-sectional view of an end effector of a second embodiment of an ultrasound medical system of the invention, wherein the end effector has an acoustic coupling medium, and wherein the end effector is adapted to change the shape of the medium-patient interface during a medical procedure, such adaptation being omitted for clarity.

In one variation of this enablement, as shown in the embodiment of FIG. 3, the transducer-distal surface 220 of the acoustic coupling medium 216 is disposable in direct contact with patient tissue. In one modification, the end effector 212 of the ultrasound medical system 210 changes the pressure exerted by the acoustic coupling medium 216 against the patient tissue when the transducer-distal surface 220 of the acoustic coupling medium 216 is disposed in direct contact with patient tissue during the medical procedure. In one construction, the medical ultrasound transducer 214 is disposed in direct contact with the transducer-proximal surface 218 of the acoustic coupling medium 216. In one application, ultrasound imaging from the medical ultrasound transducer 214 or another ultrasound transducer is used to determine the shape of the interface between the transducer-distal surface 220 of the acoustic coupling medium 216 and the patient tissue. It is noted that the interface acts as an acoustic lens surface, and that changing the shape of the interface during the medical procedure can be used to change the focus and/or the beam angle of the ultrasound emitted from the medical ultrasound transducer 214 during the medical procedure when such ultrasound non-perpendicularly passes through the interface. In one option, ultrasound strain imaging of patient tissue is performed by the ultrasound medical system 210.

In a different variation of this enablement, as shown in the embodiment of FIGS. 1-2, the end effector 112 also includes an expandable acoustic window 126 having an interior surface 128 in direct contact with the transducer-distal surface 120 of the acoustic coupling medium 116 and having an exterior surface 130 disposable in direct contact with patient tissue 124. In one modification, the end effector 112 changes the pressure exerted by the acoustic coupling medium 116 against the acoustic window 126 when the exterior surface 130 of the acoustic window 126 is disposed in direct contact with patient tissue 124 during the medical procedure. In one construction, the medical ultrasound transducer 114 is disposed in direct contact with the transducer-proximal surface 118 of the acoustic coupling medium 116. In one application, ultrasound imaging from the medical ultrasound transducer 114 or another ultrasound transducer is used to determine the shape of the interface between the transducer-distal surface 120 of the acoustic coupling medium 116 and the interior surface 128 of the acoustic window 126 and the shape of the interface between the exterior surface 130 of the acoustic window 126 and the patient tissue 124. In one variation, the acoustic window 126 is a fully-circumferential acoustic window and in another variation it is not. In one option, ultrasound strain imaging of patient tissue 124 is performed by the ultrasound medical system.

It is noted that the interfaces act as acoustic lens surfaces, and that changing the shape of the interfaces during the medical procedure can be used to change the focus and/or the beam angle of the ultrasound emitted from the medical ultrasound transducer 114 during the medical procedure when such ultrasound non-perpendicularly passes through the interfaces. In one application, the acoustic coupling medium 116 is circulating water, wherein changing the flow rate of the circulating water changes the pressure exerted by the acoustic coupling medium 116 against the acoustic window 126. It is also noted that a change in shape (such as a change in curvature) of the acoustic window 126 typically is accompanied by a change in thickness of the acoustic window 126 and a change in the distance between the medical ultrasound transducer 114 and the acoustic window 126 which can also effect focus and/or beam angle as is understood by those skilled in the art. In one implementation, the acoustic window 126 is provided with a transducer-distal surface 120 which is rippled (not shown) for use in beam angle steering as is within the level of skill of the artisan.

Figure 4:
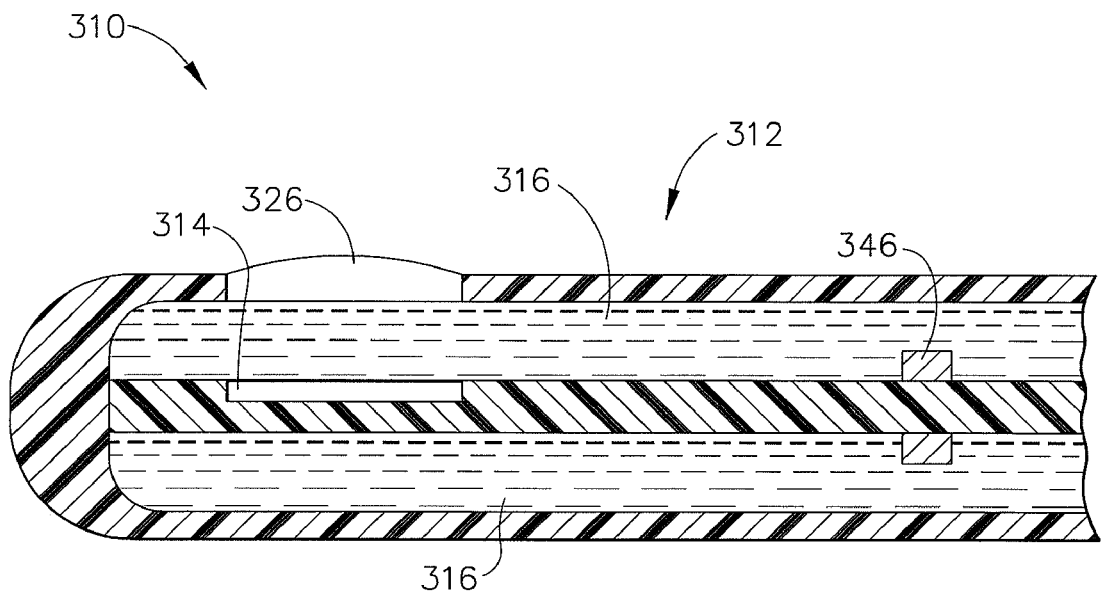
FIG. 4 is a schematic cross-sectional view of an end effector of a third embodiment of an ultrasound medical system of the invention, wherein the end effector has an acoustic window and has an acoustic coupling medium located inside the end effector, wherein the end effector is adapted to change the temperature of the acoustic coupling medium during a medical procedure, and wherein the adaptation of the end effector includes a heater.
Figure 5:
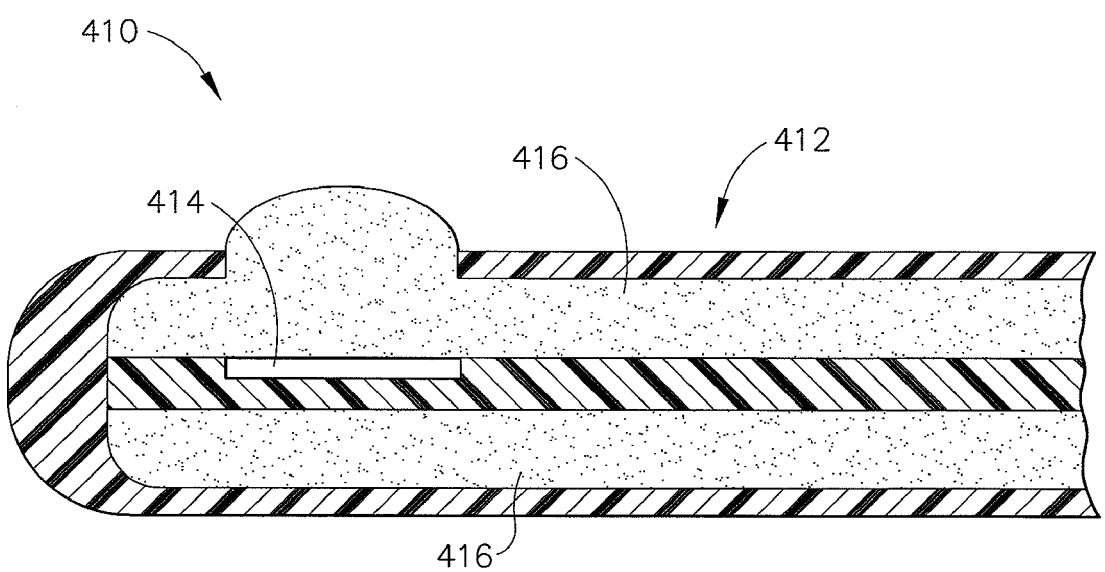
FIG. 5 is a schematic cross-sectional view of an end effector of a fourth embodiment of an ultrasound medical system of the invention, wherein the end effector has an acoustic coupling medium and is adapted to change the temperature of the acoustic coupling medium during a medical procedure, such adaptation being omitted for clarity.

In the same or a different enablement, as shown in the embodiment of FIG. 4, the at-least-one property includes temperature, and the end effector 312 of the ultrasound medical system 310 is adapted to change the temperature of the acoustic coupling medium 316 during emission, and/or between emissions, of medical ultrasound from the medical ultrasound transducer 314 during the medical procedure. Changing the temperature of the acoustic coupling medium 316 changes the speed of sound of the emitted ultrasound in the acoustic coupling medium 316 which can be used by those skilled in the art to change the focus and/or the beam angle of the emitted ultrasound when non-perpendicularly passing through a transmission medium interface. It is noted that the embodiment of FIG. 4 includes a rigid or expandable acoustic window 326, and that the embodiment of the ultrasound medical system 410 of FIG. 5 is identical to that of FIG. 4 except that the end effector 412 of FIG. 5 lacks an acoustic window.

In one example of any one or more or all of the embodiments of FIGS. 1-5, the medical ultrasound transducer 114, 214, 314 and/or 414 is chosen from the group consisting of a medical-imaging-only ultrasound transducer, a medical-treatment-only ultrasound transducer, and a medical-imaging-and-treatment ultrasound transducer. In one variation, the medical ultrasound transducer has a single transducer element having a planar or a curved ultrasound-emitting surface. In another variation, the medical ultrasound transducer has an array of transducer elements whose planar or curved ultrasound-emitting surfaces are together disposed to define a curved array surface or whose planar ultrasound-emitting surfaces are together disposed to define a planar array surface. In one modification, the transducer element array is also electronically focused and/or steered as is within the routine capabilities of those skilled in the art. In one extension, the end effector has one or more additional medical ultrasound transducers.

In the same or a different example, the acoustic coupling medium 116, 216, 316 and/or 416 is chosen from the group consisting of a liquid, a gel, and a colloid. In one variation, the acoustic coupling medium is a circulating acoustic coupling medium and in a different variation it is not circulating. Examples of liquids include, without limitation, water, a saline solution, glycerol, castor oil, and mineral oil. Other examples of liquids and examples of gels and colloids and other acoustic coupling media are left to the artisan.

In one implementation any one or more or all of the embodiments of FIGS. 1-5, the end effector 112, 212, 312 and/or 412 is disposable against an outside surface of the patient. In another implementation, the end effector is insertable into the patient.

A second expression of the embodiment of FIGS. 1-2 is an ultrasound medical system 110 comprising a controller 132 and an end effector 112. The end effector 112 includes a medical ultrasound transducer 114 and an acoustic coupling medium 116. The acoustic coupling medium 116 has a transducer-proximal surface 118 and a transducer-distal surface 120. The medical ultrasound transducer 114 is disposed to emit medical ultrasound through the acoustic coupling medium 116 from the transducer-proximal surface 118 to the transducer-distal surface 120. The end effector 112 is adapted to change at least one property of the acoustic coupling medium 116 during emission, and/or between emissions, of medical ultrasound from the medical ultrasound transducer 114 during a medical procedure on a patient 122. The controller 132 controls the end effector 112 to change the property to change ultrasound focus and/or ultrasound beam angle. In one extension of the embodiments of FIGS. 3-5, and in any one or more or all of the enablements, examples, etc. thereof, the ultrasound medical systems of FIGS. 3-5 also include the controller of the second expression of the embodiment of FIGS. 1-2.

A third expression of the embodiment of FIGS. 1-2 is an ultrasound medical system 110 comprising a controller 132 and an end effector 112. The end effector 112 includes a medical ultrasound transducer 114, an acoustic coupling medium 116, and a rigid or flexible sheath 134. The sheath 134 includes an expandable acoustic window 126. The acoustic coupling medium 116 is disposed in direct contact with the medical ultrasound transducer 114 and the acoustic window 126. The medical ultrasound transducer 114 is disposed to emit medical ultrasound through the acoustic window 126 via the acoustic coupling medium 116. The controller 132 controls the end effector 112 to change the shape of the acoustic window 126, by changing (directly or indirectly) the pressure exerted by the acoustic coupling medium 116 against the acoustic window 126, during emission, and/or between emissions, of medical ultrasound from the medical ultrasound transducer 114 during a medical procedure on a patient 122.

In one example of the third expression of the embodiment of FIGS. 1-2, a piston is used to directly change the pressure of an essentially static acoustic coupling medium. In another example, a valve is used to change the flow rate (and hence is used to indirectly change the pressure) of a flowing acoustic coupling medium. In one employment of the third expression of the embodiment of FIGS. 1-2, the controller 132 controls the end effector 112 to change the thickness of the acoustic window 126, by changing the pressure exerted by the acoustic coupling medium 116 against the acoustic window 126, during emission, and/or between emissions, of medical ultrasound from the medical ultrasound transducer 114 during a medical procedure on a patient 122.

In one arrangement of the embodiment of FIGS. 1-2, the ultrasound medical system 110 also includes a cable 136, a handpiece 138, and a rigid or flexible shaft 140. In this arrangement, the cable 136 operatively connects the controller 132 to the handpiece 138, the handpiece 138 is operatively connected to the end effector 112, and the shaft 140 supports the medical ultrasound transducer 114 and is operatively connected to the handpiece 138. The shaft 140 can be rotatable or non-rotatable with respect to the handpiece 138. Other arrangements are left to the artisan.

In one construction of the third expression of the embodiment of FIGS. 1-2, a thinner part of the sheath acts as the acoustic window. In another construction, the acoustic window is made from a different material or materials than the material or materials of the non-acoustic-window portion of the sheath. In an additional construction, the entire sheath acts as the acoustic window. Other constructions are left to the artisan.

Examples of acoustically-transmissive materials for acoustic windows include, without limitation, PET [polyethylene terephthalate] (such as 0.001-inch-thick PET for a fully-circumferential acoustic window), Nylon 6, 11 or 12, TPX [methylpentene copolymer] and flouropolymers such as PTFE [polytetrafluoroethylene], FEP [fluorinated ethylene propylene], PFA [perfluoroalkoxy], PVDA [polyvinylidene acetate], ETFE [ethylene tetrofluoroethylene], polyurethane and polyethylene (high and low density). Shaft and sheath materials, for flexible shafts and sheaths, include, without limitation, Nitinol, polyimide, reinforced polyimide, Nylon, Pebax, silicone, reinforced silicone, polyurethane, polyethylene, flouropolymers and coiled metals (e.g., coiled stainless steel).

In one deployment of the ultrasound medical system 110 of FIGS. 1-2, the end effector 112 is adapted to change the shape of the transducer-distal surface 120 of the acoustic coupling medium 116 by having the end effector 112 include an annular piston 142, movable by an attached annular piston rod 144. The movable piston 142 is used to change the pressure of a non-circulating acoustic coupling medium 116 to change the curvature of the transducer-distal surface 120 of the acoustic coupling medium 115 (which changes the curvature of the acoustic window 126). In a different deployment, not shown, the end effector 112 is adapted by having the end effector 112 include a channel for the acoustic coupling medium 116 extending from the area of the acoustic window 126 to an orifice connectable to a variable-pressure-exerting device.

In one deployment of the ultrasound medical system 310 of FIG. 4, the end effector 312 is adapted by having the end effector 312 include a heater 346 which is used to change the temperature of the acoustic coupling medium 316. In a different deployment, not shown, the end effector 312 is adapted by having the end effector 312 include a channel for the acoustic coupling medium 316 extending from the area of the acoustic window 326 to an orifice connectable to a heating device.

In a further deployment of the ultrasound medical systems of FIGS. 1-2 and FIG. 5, a tube (not shown) surrounds the shaft, is radially spaced apart from the shaft and the sheath, and longitudinally extends proximate the acoustic window with, for example, circulating water as the acoustic coupling medium which enters the ultrasound transducer-acoustic window area from the channel between the shaft and the tube and which exits the ultrasound transducer-acoustic window area from the channel between the tube and the sheath. In one variation, a pump (not shown) varies the flow rate of the water. In such adaptation of the end effector, an increasing flow rate increases the pressure of the circulating acoustic coupling medium which changes the shape of the transducer-distal surface of the acoustic coupling medium (in both the FIGS. 1-2 and FIG. 5 ultrasound medical systems) and hence the shape of the acoustic window (in the FIGS. 1-2 ultrasound medical system). Other deployments are left to the artisan.

Several benefits and advantages are obtained from one or more of the expressions of an embodiment of the ultrasound medical system of the invention. The acoustic coupling medium also acts as an acoustic lens, wherein the end effector is adapted to change at least one property (such as the shape and/or the temperature) of the acoustic coupling medium which will change the focus and/or the beam angle of emitted ultrasound, with such changes occurring during emission, and/or between emissions, of ultrasound while performing a medical procedure on a patient.

While the present invention has been illustrated by a description of several embodiments, it is not the intention of the applicants to restrict or limit the spirit and scope of the appended claims to such detail. Numerous other variations, changes, and substitutions will occur to those skilled in the art without departing from the scope of the invention. For instance, the ultrasound medical system of the invention has application in robotic assisted surgery taking into account the obvious modifications of such systems, components and methods to be compatible with such a robotic system. It will be understood that the foregoing description is provided by way of example, and that other modifications may occur to those skilled in the art without departing from the scope and spirit of the appended claims.

What is claimed is:

1. An ultrasound medical system comprising a controller and an end effector, wherein the end effector includes a sheath having an unobstructed opening to the exterior of the end effector, a medical ultrasound transducer, and an acoustic coupling gel, wherein the medical ultrasound transducer is disposed within and spaced apart from the sheath proximate the opening, wherein the acoustic coupling gel has a transducer-proximal surface disposed in direct physical contact with the medical ultrasound transducer and a transducer-distal surface which defines an acoustic lens protruding from the exterior of the end effector at the opening, wherein the medical ultrasound transducer is disposed to emit medical ultrasound through the acoustic coupling gel from the transducer-proximal surface directly to the transducer-distal surface without passing through any other acoustic coupling medium, wherein the controller is operatively connected to the acoustic coupling gel to change a property of the acoustic coupling gel to controllably change ultrasound focus and/or beam angle during emission, and/or between emissions, of medical ultrasound from the medical ultrasound transducer, and wherein the medical ultrasound transducer is aligned to direct the emissions of medical ultrasound to pass through the opening and the acoustic lens.

2. The ultrasound medical system of claim 1, wherein the gel property is a shape of the transducer-distal surface of the acoustic coupling gel and also including a movable piston disposed entirely within the sheath and in direct physical contact with the acoustic coupling gel.

3. The ultrasound medical system of claim 2, wherein the movable piston is an annular piston moved by an attached annular piston rod.

4. The ultrasound medical system of claim 1, wherein the gel property is a pressure of the acoustic coupling gel and also including a movable piston disposed entirely within the sheath and in direct physical contact with the acoustic coupling gel.

5. The ultrasound medical system of claim 4, wherein the movable piston is an annular piston moved by an attached annular piston rod.

6. The ultrasound medical system of claim 1, wherein the gel property is a temperature of the acoustic coupling gel and also including a heater disposed entirely within the sheath and in direct physical contact with the acoustic coupling gel.

7. The ultrasound medical system of claim 1, wherein the medical ultrasound transducer is chosen form the group consisting of a medical-imaging-only ultrasound transducer, a medical-treatment-only ultrasound transducer, and a medical-imaging-and-treatment ultrasound transducer.

8. The ultrasound medical system of claim 1, wherein the gel property is a shape of the transducer-distal surface of the acoustic coupling gel and wherein the end effector includes a channel for the acoustic coupling gel extending generally from the opening to an orifice adapted for connection to a variable-pressure-exerting device.

9. The ultrasound medical system of claim 1, wherein the gel property is a pressure of the acoustic coupling gel and wherein the end effector includes a channel for the acoustic coupling gel extending generally from the opening to an orifice adapted for connection to a variable-pressure-exerting device.

10. The ultrasound medical system of claim 1, wherein the medical ultrasound transducer is electronically focused and/or steered, and wherein the medical ultrasound system is operable so as to image and determine the shape of the transducer-distal surface during application of the end effector to patient tissue.

* * * * *